(12) United States Patent
Dreher (10) Patent No.: US 8,323,331 B2
(45) Date of Patent: Dec. 4, 2012

(54) RADIALLY EXPANSIBLE STENT

(75) Inventor: Gael Dreher, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 175 days.

(21) Appl. No.: 12/678,461

(22) PCT Filed: Sep. 16, 2008

(86) PCT No.: PCT/EP2008/062285
§ 371 (c)(1),
(2), (4) Date: Mar. 16, 2010

(87) PCT Pub. No.: WO2009/037245
PCT Pub. Date: Mar. 26, 2009

(65) Prior Publication Data
US 2010/0262226 A1     Oct. 14, 2010

Related U.S. Application Data

(60) Provisional application No. 61/046,314, filed on Apr. 18, 2008.

(30) Foreign Application Priority Data

Sep. 18, 2007   (GB) .................... 0718187.8

(51) Int. Cl.
*A61F 2/06* (2006.01)

(52) U.S. Cl. ..................................... 623/1.22

(58) Field of Classification Search .......... 623/1.11, 623/1.12, 1.15, 1.16, 1.17, 1.18, 1.19, 1.2, 623/1.21, 1.22; 606/108
See application file for complete search history.

(56) References Cited

U.S. PATENT DOCUMENTS 6,214,039 B1   4/2001   Banas et al.
(Continued)

FOREIGN PATENT DOCUMENTS

EP   1447057 A1   8/2004
(Continued)

OTHER PUBLICATIONS

Dec. 4, 2008 International Search Report in international application No. PCT/EP2008/062285 filed on Sep. 16, 2008.
(Continued)

*Primary Examiner* — Ryan Severson
*Assistant Examiner* — Jonathan W Miles
(74) *Attorney, Agent, or Firm* — Rutan & Tucker, LLP (57) ABSTRACT

There is disclosed herein a radially expansible stent formed from a tube, comprising a continuous spiral of tube material with a plurality of turns (30, 32) wrapping about a longitudinal axis from a first end of the stent to a second end of the stent, the spiral including a plurality of struts (40, 42) in a zig-zag arrangement joined at points of inflection (44), wherein each strut includes a double bend (46) remote from a point of inflection (44) and first (58, 60) and second (62, 64) length portions on opposite sides of the double bend (46); adjacent struts (40, 42) have handed double bends that are substantially mirror images of one another, the handed double bends facing each other such that in a stent collapsed configuration the length portions (58, 60) of adjacent struts on a first side of the double bends (46) are spaced closer than the length portions (62, 64) of adjacent struts on a second side of the double bends (46) opposite the first side, the adjacent struts on said first side of the double bends being joined at a point of inflection (44); and each point of inflection (44) on said first side of the double bends (46) on one turn (30) of the continuous spiral lying between adjacent struts on said second side of the double bends (46) on the next turn (32) of the continuous spiral. A method of forming such a stent is also disclosed.

14 Claims, 5 Drawing Sheets

U.S. PATENT DOCUMENTS

| | | | |
|---|---|---|---|
| 6,383,214 B1 | 5/2002 | Banas et al. | |
| 6,451,047 B2 | 9/2002 | McCrea et al. | |
| 6,579,314 B1 | 6/2003 | Lombardi et al. | |
| 6,663,664 B1 * | 12/2003 | Pacetti | 623/1.2 |
| 6,712,846 B1 | 3/2004 | Kraus et al. | |
| 6,878,162 B2 | 4/2005 | Bales et al. | |
| 6,911,041 B1 | 6/2005 | Zscheeg | |
| 8,043,358 B2 * | 10/2011 | Weber et al. | 623/1.15 |
| 2003/0060869 A1 | 3/2003 | Feeser et al. | |
| 2004/0044401 A1 | 3/2004 | Bales et al. | |
| 2007/0032860 A1 | 2/2007 | Brooks et al. | |
| 2007/0106369 A1 | 5/2007 | Brown et al. | |
| 2007/0112408 A1 | 5/2007 | Meens et al. | |

FOREIGN PATENT DOCUMENTS

| | | |
|---|---|---|
| EP | 1707162 A1 | 10/2006 |
| WO | 0139695 A2 | 6/2001 |
| WO | 2006029617 A1 | 3/2006 |
| WO | 2007095466 A2 | 8/2007 |

OTHER PUBLICATIONS

Mar. 18, 2010 Written Opinion of the ISA in international application No. PCT/EP20081062285 filed on Sep. 16, 2008.

Mar. 18, 2010 International Preliminary Report on Patentability in international application No. PCT/EP2008/062285 filed on Sep. 16, 2008.

* cited by examiner

RADIALLY EXPANSIBLE STENT

PRIORITY

This application is a U.S. national stage application under 35 USC §371 of International Application No. PCT/EP2008/062285, filed Sep. 16, 2008, claiming priority from British Patent Application No. GB 071 8187.8, filed 18 Sep. 2007, and U.S. U.S. Provisional Patent Application No. 61/046,314, filed 18 Apr. 2008, each of which is incorporated by reference in its entirety into this application.

TECHNICAL FIELD

This invention relates to a radially expansible stent made from a tube of stent material, which exhibits a continuous zig-zag spiral of material which wraps around the lumen of the stent in a plurality of turns, advancing from near one end of the stent to near the other end, the zig-zags being composed of struts joined at points of inflection.

BACKGROUND ART

Ever since Dotter proposed to use a simple wire spiral as a stent, it has been known to build a stent from a spiral pattern of stenting material. One way to move from a relatively small stent diameter to a relatively large diameter, when the stent is a spiral, is for the number of turns of the spiral to go down, as the diameter goes up. Another way is to build the spiral from a succession of zig-zag struts. In a radially compact (unexpanded) configuration, the struts can all lie more or less parallel with the longitudinal axis of the stent, with the points of inflection at each end of each strut of the zig-zag causing the line of strut material to double-back on itself to extend around an angle of 180° into the respective adjacent struts on either side. A very substantial radial expansion can be achieved by opening up the zig-zags, so that the struts no longer lie parallel to each other and with the long axis of the stent but, rather, in a more open zig-zag, where the angle between two succeeding struts of the zig-zag, at the intervening point of inflection, is more like 120° than the original 180°. One example of such a stent is disclosed in U.S. Pat. No. 6,911,041 B1.

One big advantage of a spiral pattern for a stent is that it is a great deal more flexible in bending than a simple annular cage of struts such as one finds in the early Palmaz stent. However, the price of such great flexibility is that the stenting force available from a spiral stent, to push bodily tissue away from the long axis of the stent, is liable to be inherently significantly less than with a cage stent.

Various spiral pattern stents are known from WO 2007/095466 A2, as well as in the prior art citations acknowledged therein.

It would be desirable to be able to retain the flexibility of a spiral stent yet achieve, at the same, enhanced magnitude radially outwardly directed stenting forces.

SUMMARY OF THE INVENTION

According to a first aspect of the present invention, there is provided a radially expansible stent formed from a tube, comprising a continuous spiral of tube material with a plurality of turns wrapping about a longitudinal axis from a first end of the stent to a second end of the stent, the spiral including a plurality of struts in a zig-zag arrangement joined at points of inflection, wherein: each strut includes a double bend remote from a point of inflection and first and second length portions on opposite sides of the double bend; adjacent struts have handed double bends that are substantially mirror images of one another, the handed double bends facing each other such that in a stent collapsed configuration the length portions of adjacent struts on a first side of the double bends are spaced closer than the length portions of adjacent struts on a second side of the double bends opposite the first side, the adjacent struts on said first side of the double bends being joined at a point of inflection; and each point of inflection on said first side of the double bends on one turn of the continuous spiral lying between adjacent struts on said second side of the double bends on the next turn of the continuous spiral.

According to a second aspect of the present invention, there is provided a method of forming a radially expansible stent, comprising: providing a tube of nitinol material; and cutting the tube with a beam jet into a pattern of continuous spiral with a plurality of turns wrapping about a longitudinal axis, the spiral including a plurality of struts in a zig-zag arrangement joined at points of inflection, each strut including a double bend remote from a point of inflection and first and second length portions on opposite sides of the double bend, adjacent struts having handed double bends that are mirror images of one another, the handed double bends facing each other such that in a stent unexpanded configuration the length portions of adjacent struts on a first side of the double bends are spaced closer than the length portions of adjacent struts on a second side of the double bends opposite the first side, the adjacent struts on said first side of the double bends joined at a point of inflection, each point of inflection on said first side of the double bends on one turn of the continuous spiral lying between adjacent struts on said second side of the double bends of the next turn of the continuous spiral.

According to a third aspect of the present invention, there is provided a radially expansible stent made from a tube of stent material, which exhibits a continuous zig-zag spiral of material which wraps around the lumen of the stent in a plurality of turns, advancing from near one end of the stent to near the other end, the zig-zags being composed of struts joined at points of inflection characterized in that each said strut includes a handed double bend located remote from the points of inflection at each end of the strut, succeeding struts of the zig-zag exhibiting double bends that are alternately left-handed and right-handed so that, in a radially unexpanded configuration of the stent, a left-handed double bend faces a right-handed double bend and the length portions of the respective struts to one side of the facing double bends are side by side whereas the length portions of the said two respective struts on the other side of the double bends are spaced apart and further characterized in that the turns of the zig-zag spiral overlap, in the sense that each point of inflection of one turn lies between the space apart length portions of two struts of the next adjacent turn.

A stent according to the invention thus may comprise a plurality of struts extending generally in the stent axial direction and arranged adjacent to one another to approximate a cylindrical mesh formed about the stent longitudinal axis. The struts may be approximately the same length as each other, with adjacent struts being alternately longer and shorter than each other to create an axial offset in one axial direction so as to form an axially stepped pattern as one moves successively from one strut to the next around the stent axis, to give the desired helical profile. The spiral helix of the stent material so formed can be a continuous thread of stent material that runs unbroken from one axial end of the spiral to the other axial end, the adjacent struts being joined alternately at one axial end and then at the other axial end to the preceding and successive struts in the series as one moves from strut to strut in one rotational direction about the stent axis. The joints between adjacent struts form points of inflection at the strut ends. These points of inflection are tight curves and may be of a similar width to the struts. In the compact, unexpanded state, for example when first cut from a tube of stent material, the points of inflection curve around an angle of 180° to join together the two adjacent struts that lie substantially parallel to each other. When the stent expands to a larger diameter, the adjacent struts separate laterally, but remain joined at the points of inflection, so that they must rotate relative to each other (like when opening a pair of compasses). The angle around the point of inflection then decreases to less than 180°, to maybe 120° at the expanded diameter.

By overlapping the turns of the zig-zag spiral, it is possible to achieve a greater density of stent struts per unit area of surface of the bodily lumen that is to be stented by the stent. Clearly, the more of the resilient stent material that is available to press the bodily tissue outwardly, away from the longitudinal axis of the lumen, the more stenting force can be delivered. The present invention provides a way of overlapping the succeeding turns of the zig-zag spiral, to increase stenting force, without at the same time prejudicing the objective of full bending flexibility.

Furthermore, the spiral zig-zag stent of the present invention is remarkably easy to manufacture, using the by now well-known beam jet (normally a laser) cutting techniques successfully used in a range of already commercially successful stent designs.

As we can see below in illustrated embodiments, it is convenient to locate the inventive double bend midway along the struts in which they are located. In an archetypal design of the present invention, the as-cut struts in the radially compact disposition of the stent will all lie substantially parallel to each other and to the longitudinal axis of the stent (except for the portion of the length of each strut that constitutes the double bend). As the stent expands to its radially expanded working disposition, the points of inflection will bend to allow the struts to rotate relative to each other about the points of inflection at each end, and relative to the long axis of the stent, to take up their zig-zag dispositions at an oblique angle to the long axis of the stent.

The stresses to which the struts are subject, during delivery to the stenting site and during expansion at that site to stent the bodily lumen, will normally not be such as to deform the double bend out of existence, so that inspection of the stent in its finished, radially expanded configuration, will reveal the continuing presence of the double bends.

An interesting question arises at the axial ends of a stent when the stenting struts are arranged in a spiral configuration. The spiral will end in a free end of the final strut. Rather than have that free end protruding from the annulus of struts which is the stent, it will generally be desirable to have final strut of the spiral arrangement pointing back towards the middle of the stent spiral, and the other end of the spiral. In that way, there is less likelihood of the cantilevered free end of the final strut puncturing or otherwise damaging bodily tissue on which the stent end impinges. Other arrangements will be known to those skilled in the art, for managing the stresses at the opposed ends of the spiral and for terminating the spiral at each end.

BRIEF DESCRIPTION OF THE DRAWINGS

To enable a better understanding of the present invention, and to show how the same may be carried into effect, reference will now be made, by way of example only, to the accompanying drawings, in which.

DETAILED DESCRIPTION

Figure 1:
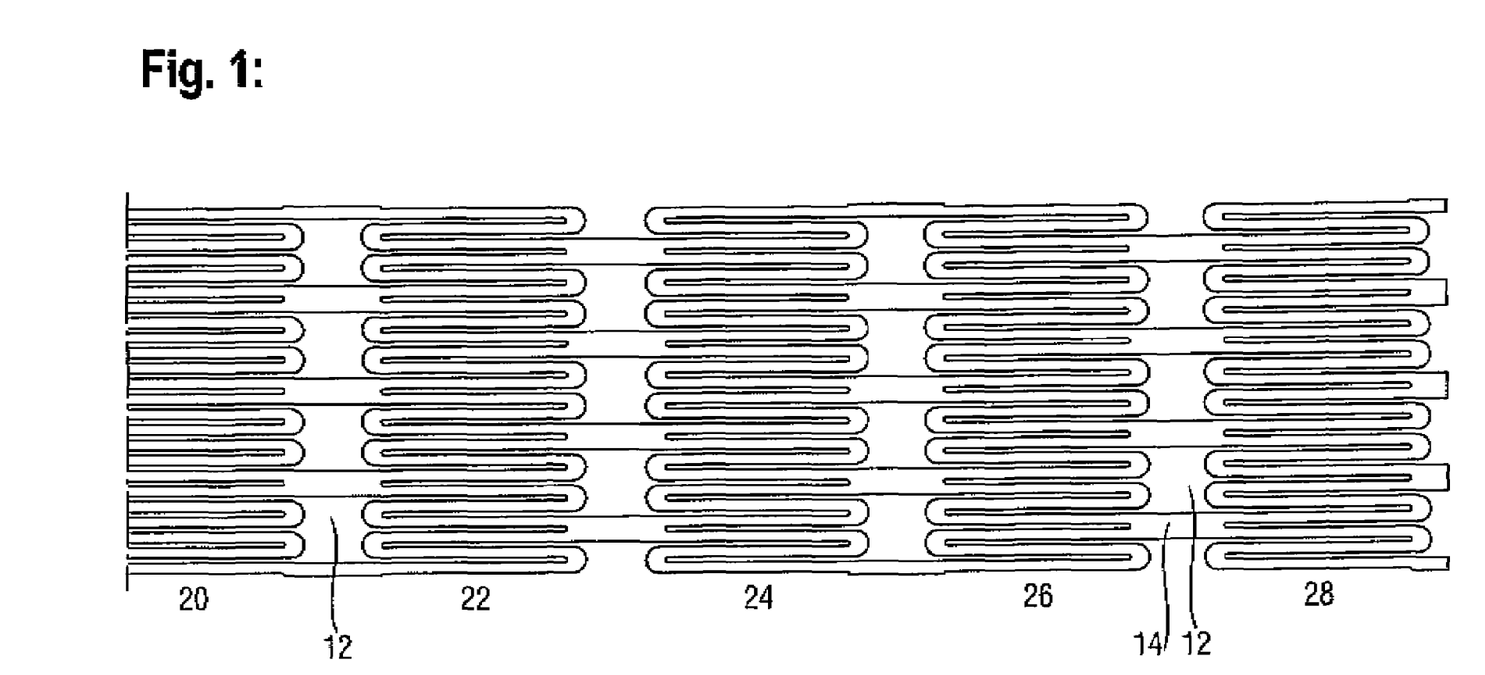
FIG. 1 is a view of a prior published stent design, laid flat

Referring to FIG. 1, there is shown a stent matrix, laid flat, such as is created using the teachings of an earlier patent publication of the present applicant, WO-A-2001/032102. A laser cuts narrow slits in a tubular workpiece of nickel-titanium shape memory alloy, the multitude of slits all being parallel to the longitudinal axis of the workpiece. Scrap portions are removed from the workpiece to leave apertures 12 in the slitted workpiece. The apertures are flanked by connector portions 14 between successive zig-zag rings 20, 22, 24, 26 and 28 of the stent, succeeding rings being connected to each other by a set of four bridges 14 arranged at 90° intervals around the circumference of the stent workpiece. While each of the stenting rings 20 to 28 can deliver a substantial stenting force to bodily tissue outside the respective ring, the set of four bridges 14 between two adjacent stenting rings can limit the flexibility of the stent matrix, in bending, after deployment.

Figure 2:
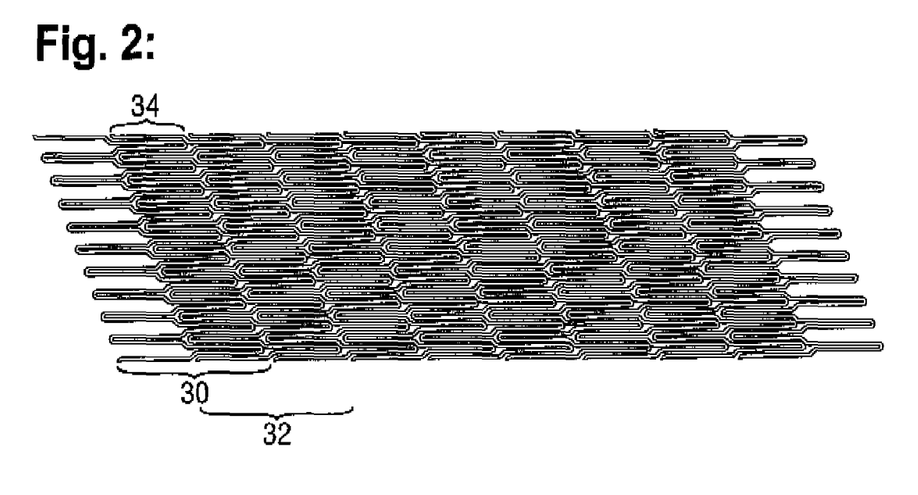
FIG. 2 is a view of a stent matrix design in accordance with the present invention, also laid flat as in FIG. 1

Turning to FIG. 2, one immediately recognizes similarities and differences between FIG. 1 and FIG. 2. One similarity is that the tubular workpiece can be converted to a functioning state by the use of a laser to cut a multitude of slits in the workpiece, the slits extending through the full wall thickness of the workpiece and all being substantially parallel to the length direction of the workpiece. The main difference is that the overall architecture of the stent matrix is that of a spiral rather than of a succession of stenting rings disposed transverse to the length direction of the workpiece.

Careful inspection of FIG. 2 will reveal that the turns of the spiral are interlaced. Thus, a first turn of the spiral can be recognized as corresponding to reference 30, in which case the second turn of the spiral is embraced by reference 32, with almost half the length of the struts of these two spirals overlapping, in the overlap region 34. The ability of the struts of each turn of the spiral, to accommodate in overlap the succeeding zig-zags of the next adjacent turn of the spiral, is accomplished by a "double bend" or "slalom" feature midway along the length of each strut that makes up the zig-zag. To see this better, we turn to FIG. 3, which shows a small detail of the complete matrix shown in FIG. 2.

Figure 3:
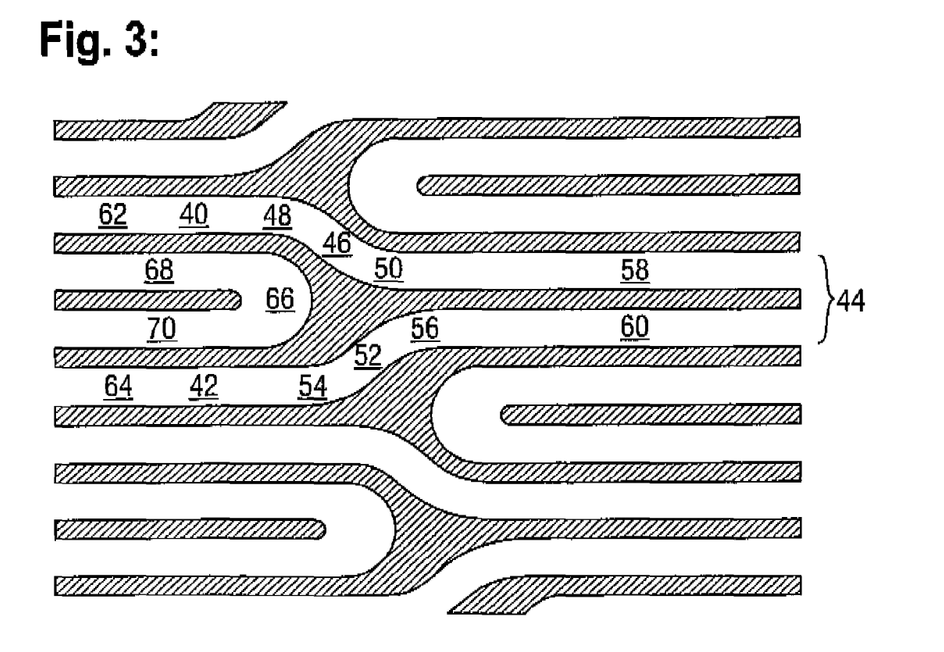
FIG. 3 is a detail from FIG. 2

Looking at FIG. 3, we can see part of a first strut 40 and a second strut 42, that are connected at a point of inflection which is outside the field of FIG. 3, beyond the right-hand margin, indicated by reference 44. Midway along the length of strut 40 is a portion 46 of the length of strut 40 which is not parallel to the long axis of the tubular stent. It lies between a first bend 48 and a second bend 50 which curve in opposite directions and together make up the slalom or double bend portion midway along the length of strut 40. The double bend or slalom is characterized by the first and second bends 48 and 50 being closely spaced, rather than separated by any substantial straight section of strut.

There is a similar double bend feature 52 midway along the length of strut 42, between corresponding bend portions 54 and 56. The respective double bend portions 46 and 52 are "handed" (left-handed and right-handed) in the sense that they are in mirror image to each other rather than being parallel to each other. The consequence is that length portions 58 and 60 of struts 40 and 42 lie side by side to each other, separated only by the width of the beam that cut the slit between them. Conversely, length portions 62 and 64 of the adjacent struts 40 and 42 lie spaced apart from each other, by double the distance by which a double bend portion displaces the length of its strut laterally, i.e. circumferentially, with respect to the longitudinal axis of the stent.

As the reader will already have appreciated, the gap between length portions 62 and 64 accommodates the point of inflection 66 and side by side length portions 68 and 70 of a zig-zag of the next adjacent turn around the circumference of the stent of the spiral stent matrix. This pattern is repeated throughout the spiral stent matrix and one can see even from the FIG. 3 detail that there is an absence of bridges between succeeding turns of the spiral and that the zig-zags of the successive turns of the spiral are densely packed. The arrangement thereby can accomplish the objectives of the invention, namely, to preserve flexibility in bending but also to offer a densely enough packed arrangement of struts as to provide substantial stenting force to bodily tissue outside the annulus of the stent. The bending flexibility is enjoyed not only during trans-luminal catheter delivery of the stent but also after release at the stenting site, with the stent in its finished, radially expanded configuration. Suitable delivery devices and methods are disclosed and discussed, for example, in EP 1447 057 A1, US Patent Application No. US 2007/032860 A1, US Patent Application No. US 2003/060869 A1, or US Patent Application No. 2007/0112408 A1.

Figure 4:
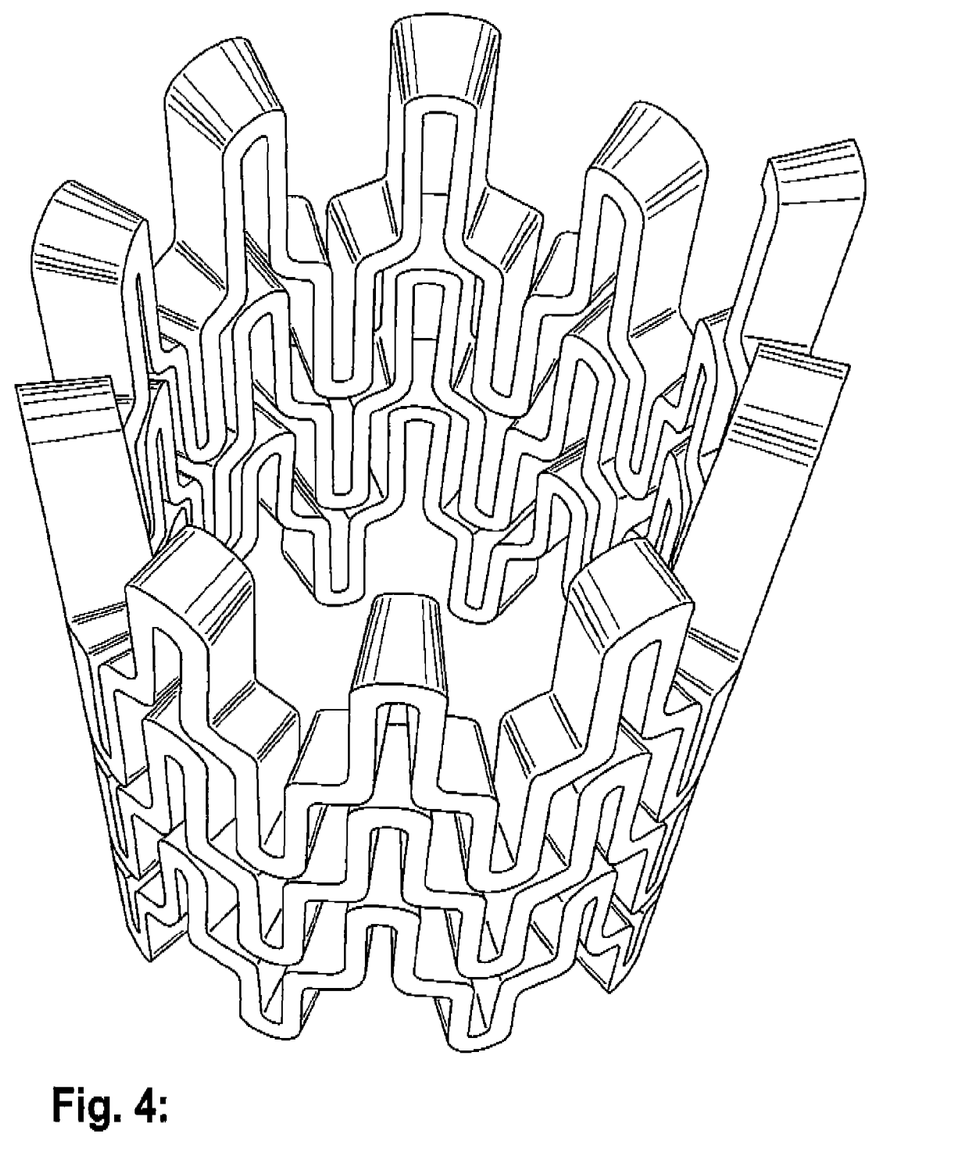
FIG. 4 is an isometric view of a stent matrix as seen, laid flat, in FIG. 2.
Figure 5:
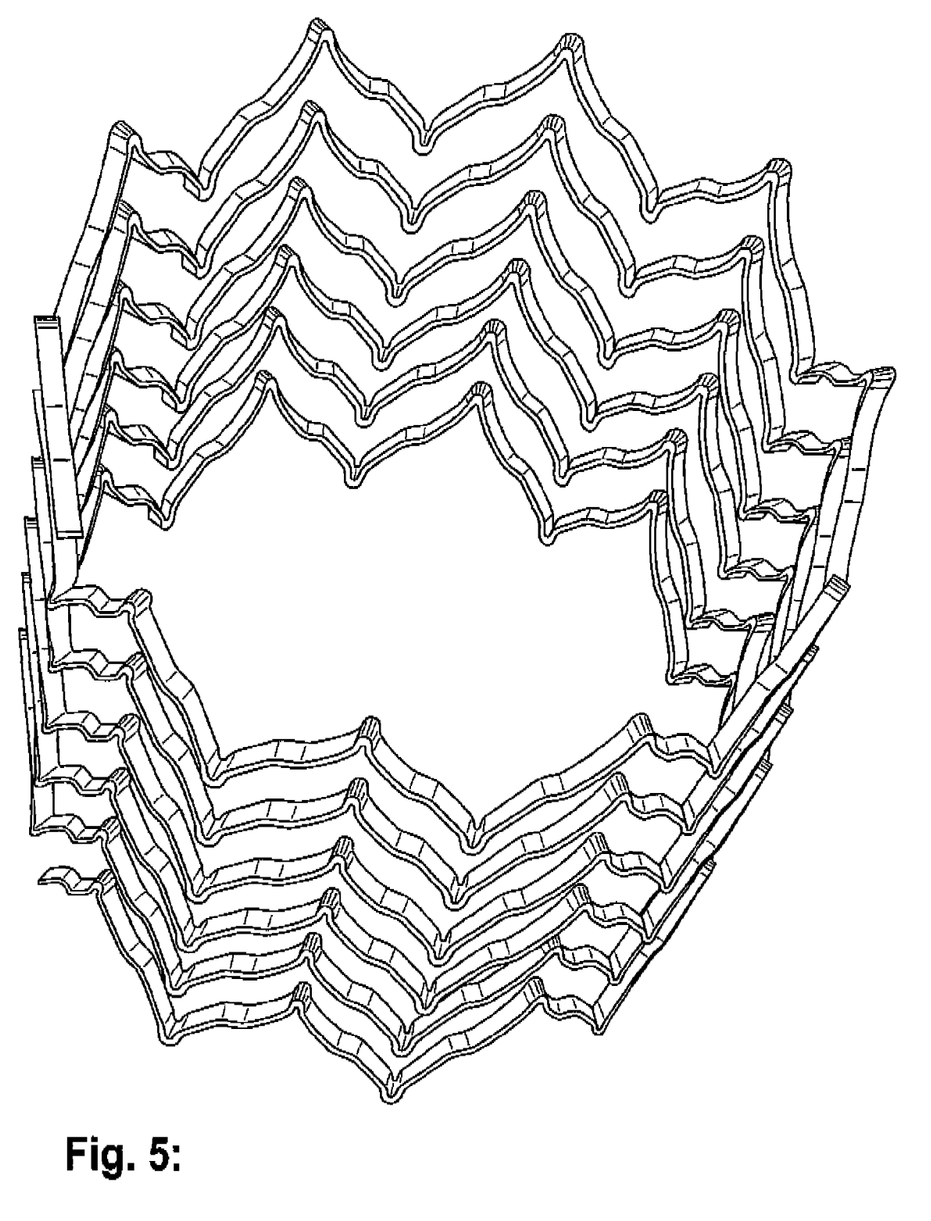
FIG. 5 is an isometric view of the FIG. 4 stent arrangement, but in its radially expanded configuration.

Turning now to FIGS. 4 and 5, we find no new information but simply three dimensional representations of the stent of FIGS. 2 and 3, first (FIG. 4) in the "as cut" radially compact configuration in which the tubular workpiece is cut with a laser and in which it is translucminally delivered on a catheter to the stenting site within the body of the patient. By contrast, FIG. 5 shows the FIG. 4 stent duly expanded radially at the stenting site, released from its catheter delivery system, with the zig-zags opened out to achieve a much greater diameter than is evident in FIG. 4. The reader will notice that the struts of the opened out zig-zag pattern still display the "double bend" feature midway along their length. This is not an essential part of the invention but, equally, it is not a disadvantage of the relatively simple manufacturing process of the illustrated embodiment of the present invention that double bends remain after the stent has expanded.

Figure 6:
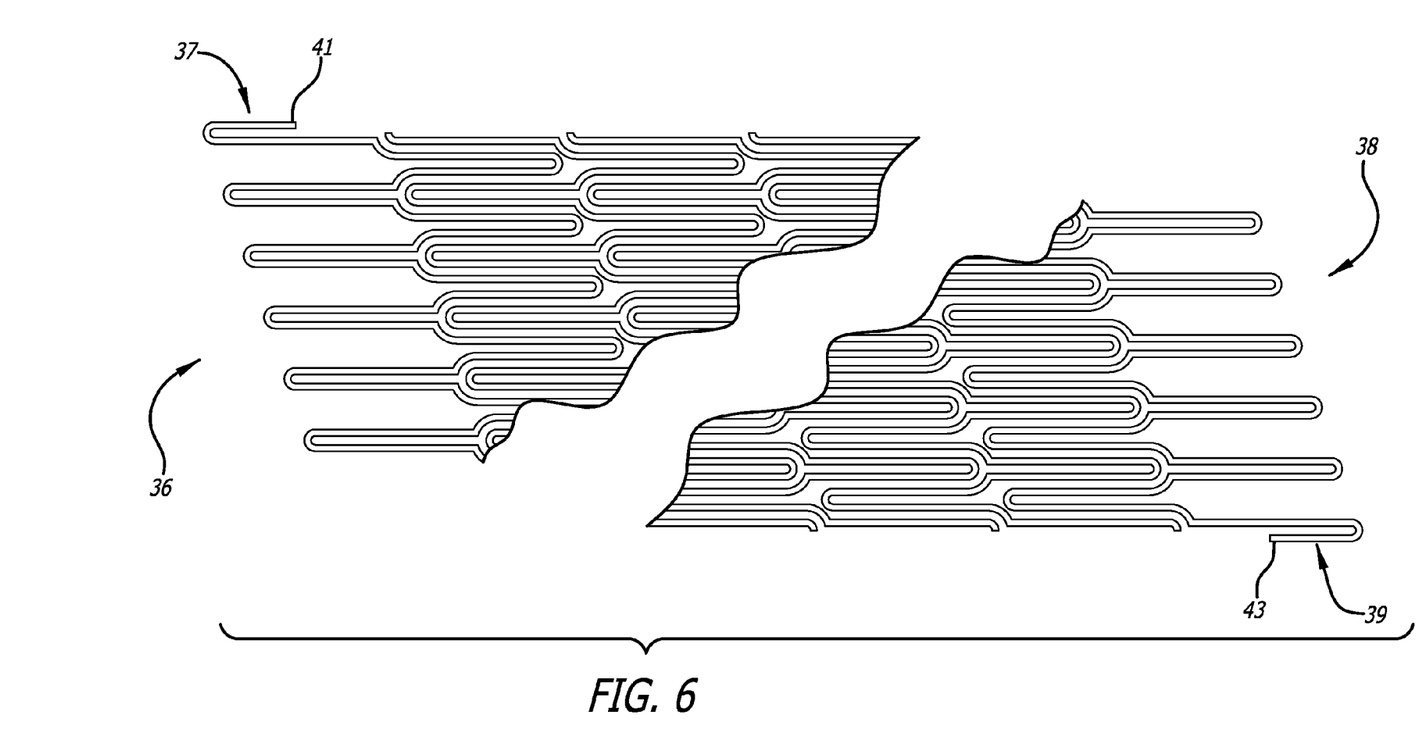
FIG. 6 is an expanded view of portions of the ends of the FIG. 2 stent.

Turning to FIG. 6, we see an expanded view of FIG. 2 for both the first terminal end 36 and the second terminal end 38. This view illustrates the aforementioned embodiment in which the final strut 37 of the spiral arrangement at the first terminal end 36 has a free end 41 that points back towards the middle of the stent spiral (i.e., toward the second terminal end 38), and in which the final strut 39 of the spiral arrangement at the second terminal end 38 has a free end 43 that points back towards the middle of the stent spiral (i.e., toward the first terminal end 36). As discussed, such a configuration reduces the likelihood of the cantilevered free ends of the final struts puncturing or otherwise damaging bodily tissue on which the stent end impinges.

The inventor can envisage a system in which shape memory alloy is heat-treated to remember an expanded configuration that does not display double bends, yet can be compressed into a radially compact disposition with double bends to accommodate the overlaps of the spiral. However, the inventor does not see that such a prosthesis would be so straightforward to design and build, and does not see enough advantages from eliminating the double bends in the deployed configuration, that would make the additional complications of design and manufacture worthwhile. Nevertheless, included within the scope of the present invention are devices which no longer display double bends in the radially expanded configuration. In particular, the form of the spiral stent of the present invention is not facile to replicate except by the laser beam jet method proposed herein, other stent-formation techniques being found to be more complicated and expensive or time-consuming. The benefits of beam jet cutting are thus realized to a high degree with the spiral stent of the present invention, which speaks against the introduction of largely unnecessary additional complications (although the possibility to do so is, of course, recognized).

Although the illustrated embodiment is described in terms of a nickel-titanium shape memory alloy, such a material is not a necessary feature of the present invention, which can equally well be embodied in balloon expandable stents of stainless steel or indeed any stent whether it undergoes plastic deformation in being deployed, or elastic deformation, or the quasi-elastic deformation of nickel-titanium shape memory alloys. Suitable materials for stents and stent coverings are discussed in WO2007/095 466 A2, and in the prior art citations referenced therein.

Although the specific description has been in terms of a bare uncovered stent, the invention is likely to have a particular application in the field of covered stents and stent grafts. The present applicant has particular expertise in covering nickel-titanium shape memory alloy stents with expanded PTFE coverings, for example as disclosed in US Patent Application No. US 2001/039 446 A1, U.S. Pat. No. 6,214,039 B1, U.S. Pat. No. 6,579,314 B1, or U.S. Pat. No. 6,383,214 B1, but coverings of other materials are known and are feasible with the present stent matrix. Coverings may be particularly useful for cladding the opposite end portions of the spiral, shielding bodily tissue from possible damage by those spiral ends.

Increasingly, stents are drug-eluting or coated with an active agent or drug. It is contemplated that stents in accordance with the present invention will include drug-eluting or coated stents. Such a stent is disclosed, for example, in U.S. Pat. No. 6,712,846 B1.

Although stents are mostly used in vascular applications, whether coronary or peripheral, there are many other bodily lumens that can benefit from stenting, for example biliary applications. These are also contemplated with the stent matrix of the present invention, which will find particular application whenever a high degree of flexibility after deployment is required.

Stents often carry radiopaque markers, usually at each end of the stent annulus. In stents of the present invention, an attractive location for such markers is the stent spiral ends. The markers could be placed as wide area paddles or spoons, again to blunt the otherwise pointed end and so shield bodily tissue from damage.

In other embodiments, it may be attractive to provide at each end of the zig-zag spiral a loop at material (such as an endless zig-zag stenting ring) around the lumen of the stent, and attach each spiral end to one of these end loops. In that case, it may well be desirable to connect the spiral to the end loop at a small number (2 to 5, maybe 6) locations around the circumference of the lumen, to preserve the relative orientations and locations of the three components of the loop-spiral-loop assembly.

Other embodiments will be evident to those skilled in the art.

All publications and patent applications cited in this specification are herein incorporated by reference in their entirety as if each individual publication or patent application were specifically and individually put forth herein.

The invention claimed is:

1. A radially expansible stent formed from a tithe, comprising a continuous spiral of tube material with a plurality of turns wrapping about a longitudinal axis from a first end of the stent to a second end of the stent, the spiral including a plurality of struts in a zig-zag arrangement joined at points of inflection, wherein along a section between the first end of the stent and the second end of the stent:
- each strut includes a double bend remote from a point of inflection and first and second length portions on opposite sides of the double bend;
- adjacent struts have handed double bends that are substantially mirror images of one another, the handed double bends facing each other such that in a stent collapsed configuration the length portions of adjacent struts on a first side of the double bends are spaced closer than the length portions of adjacent struts on a second side of the double bends opposite the first side, the adjacent struts on said first side of the double bends being, joined at a point of inflection;
- in said stent collapsed configuration all said length portions lie parallel to each other and to the longitudinal axis of the stent; and
- each point of inflection on said first side of the double bends on one turn of the continuous spiral lying between adjacent struts on said second side of the double bends on the next turn of the continuous spiral.

2. The radially expansible stent according to claim 1, wherein the majority of the length portions of adjacent struts on said first side of the double bends lies between adjacent struts on said second side of the double bends.

3. The radially expansible stent according to claim 1, wherein the double bend is midway along the length of each strut.

4. The radially expansible stent according to claim 1, wherein the stent includes a first terminal end having a turn of the spiral with spaces between adjacent struts on said second side of the double bends unoccupied by points of inflection.

5. The radially expansible stent according to claim 1, wherein the double bends remain present in a stent expanded configuration.

6. The radially expansible stent according to claim 1, wherein the continuous spiral includes a first stmt, having a free end located at a first terminal end of the stent, the first strut free end pointing toward a second, terminal end of the stent opposite the first terminal end.

7. The radially expansible stent according to claim 6, wherein the second terminal end of the stent includes a second strut having a free end, the second strut free end pointing toward the first terminal end.

8. The radially expansible stent according to claim 1, wherein the continuous spiral includes a first stmt, having a free end located at a first terminal end of the stent and a second strut having a free end located at a second terminal end of the stent, each of the first and second strut free ends covered by a covering material.

9. A radially expansible stent made from a tube of stent material, which exhibits a continuous zig-zag spiral of material which wraps around the lumen of the stent in a plurality of turns, advancing from near one end of the stent to near the other end, the zig-zags being composed of struts joined at points of inflection, wherein along a section between the one end of the stent and the other end of the stent:
- each said strut includes a handed double bend located remote from the points of inflection at each end of the strut and between two length portions of the strut that are parallel to each other and when the stent is radially minimized, parallel to the longitudinal axis of the stunt tube, succeeding struts of the zig-zag exhibit double bends that are alternately left-handed and right-handed so that, in a radially unexpanded configuration of the stent, a left-handed double bend faces a right-handed double bend and the length portions of the respective struts to one side of the facing double bends are side by side whereas the length portions of the said two respective struts on the other side of the double bends are spaced apart, and wherein
- the turns of the zig-zag spiral overlap, in the sense that each point of inflection of one turn lies between the spaced apart length portions of two struts of the next adjacent turn.

10. The radially expansible stent according to claim 9, wherein the double bend is midway along the length of the strut in which it is located.

11. The radially expansible stent according to claim 9, wherein the strut design is obtainable by a beam jet cutting technique.

12. The radially expansible stem according to claim 9, that is expansible from a radially compact to a radially expanded configuration and wherein the struts in the radially compact configuration lie substantially parallel to the longitudinal axis of the stent, except the portion of the length of each strut that lies within the double bend.

13. The radially expansible stent according to claim 9, wherein the double bend remains present in the radially expanded configuration of the stent.

14. The radially expansible stent according to claim 9, wherein the spiral ends in a strut that extends from its point of inflection with the remainder of the spiral in a direction generally towards the other end of the spiral.

* * * * *

UNITED STATES PATENT AND TRADEMARK OFFICE
CERTIFICATE OF CORRECTION

| | | |
|---|---|---|
| PATENT NO. | : 8,323,331 B2 | Page 1 of 1 |
| APPLICATION NO. | : 12/678461 | |
| DATED | : December 4, 2012 | |
| INVENTOR(S) | : Gael Dreher | |

It is certified that error appears in the above-identified patent and that said Letters Patent is hereby corrected as shown below:

Claim 1, column 7, line 7, delete "tithe" and insert --tube--.
Claim 1, column 7, line 24, delete "," after "being".
Claim 6, column 7, line 50, delete "stmt," and insert --strut--.
Claim 6, column 7, line 50, delete "," after "second".
Claim 8, column 8, line 6, delete "stmt," and insert --strut--.
Claim 9, column 8, line 22, delete "stunt" and insert --stent--.

Signed and Sealed this
Twenty-ninth Day of January, 2013

David J. Kappos
*Director of the United States Patent and Trademark Office*